United States Patent [19]

Todd et al.

[11] Patent Number: 5,256,811

[45] Date of Patent: Oct. 26, 1993

[54] CERTAIN INTERMEDIATES FOR THE PREPARATION OF NEUINIC ACID DERIVATIVES

[75] Inventors: Richard S. Todd, Buckinghamshire; Maxwell Reeve, Oxford, both of England

[73] Assignee: British Bio-Technology Limited, Oxford, United Kingdom

[21] Appl. No.: 804,075

[22] Filed: Dec. 6, 1991

[30] Foreign Application Priority Data

May 23, 1991 [GB] United Kingdom ............ 9111192.2

[51] Int. Cl.$^5$ .................. C07C 321/22; C07C 69/608
[52] U.S. Cl. ...................... 560/10; 560/100; 560/106; 560/119
[58] Field of Search ................. 560/119, 106, 100, 10

[56] References Cited

U.S. PATENT DOCUMENTS

| 3,271,365 | 9/1966 | Parham et al. | 560/119 |
| 4,889,947 | 12/1989 | Phalangas et al. | 560/119 |

*Primary Examiner*—C. Warren Ivy
*Assistant Examiner*—Ba K. Trinh
*Attorney, Agent, or Firm*—Allegretti & Witcoff

[57] ABSTRACT compounds of formula I

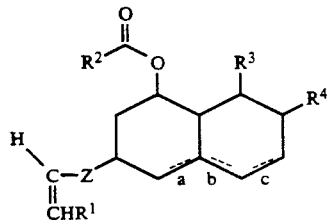

wherein $R^1$ represents a $C_{1-8}$ alkyl, $C_{2-8}$ alkenyl, $C_{2-8}$ alkynyl, $C_{3-8}$ cycloalkyl($C_{1-8}$)alkyl, $C_{1-8}$ hydroxyalkyl, $C_{1-8}$ alkylthio, phenyl or substituted phenyl;

$R^3$ represents a $C_{1-8}$ alkyl, $C_{2-8}$ alkenyl, $C_{2-8}$ alkynyl, $CO_2(C_{1-8})$alkyl, $CO_2(C_{2-8})$ alkenyl, $C_{1-8}$ alkylthio, $(C_{1-2})$alkyl $CO_2(C_{1-8})$ alkyl or $C_{1-8}$ aldehydroalkyl where the aldehyde function is protected by a suitable protecting group (for example, an acetal such as a dimethyl acetal);

$R^4$ represents a hydrogen atom, $C_{1-8}$ alkyl or $C_{2-8}$ alkenyl;

Z represents a group $(CH_2)_n$ or a branched alkyl chain; n is 1 to 8;

and each of a, b and c is independently a single or a double bond;

can be prepared relatively easily and in good xxx at room temperature by reacting a compound of general formula II

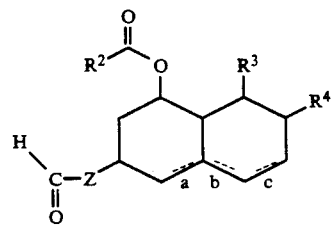

wherein $R^2$, $R^3$, $R^4$, Z, a, b and c are as define din general formula I; with a compound of general formula III $$CHI_2R^1 \qquad (III)$$

wherein $R^1$ is as defined in general formula I;
in the presence of metal ions such as chromium (II) ions. The sever conditions of the Wittig reaction can therefore be avoided.

Compounds of formula I are useful intermediates in the synthesis of mevinic acids, which are potent inhibitors of HMG-CoA reductase and which are useful in the treatment of hypocholesterolaemia an hyperlipidaemia.

2 Claims, No Drawings

CERTAIN INTERMEDIATES FOR THE PREPARATION OF NEUINIC ACID DERIVATIVES

BACKGROUND OF THE INVENTION

1. Field of the Invention

This invention relates primarily to novel synthetic procedures and compounds which are useful in the synthesis of a range of mevinic acids.

2. Description of the Prior Art

A number of mevinic acids which can formally be regarded as decalin derivatives, have been reported to be potent inhibitors of the enzyme 3-hydroxy-3-methylglutaryl coenzyme A (HMG-CoA reductase), the rate limiting enzyme in the biosynthesis of cholesterol in mammals including man, and as such are useful in the treatment of hypercholesterolaemia and hyperlipidaemia.

Thus W F Hoffman et al (J. Med. Chem., 29, 849–852 (1986)) have reported the synthesis and testing of a compound now known as simvastatin, having the structure

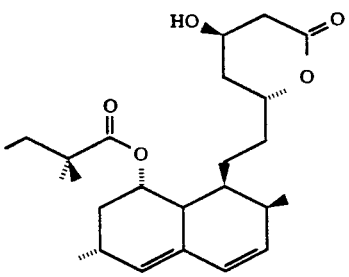

EP-A-0251625 (Inamine) discloses compounds of structure

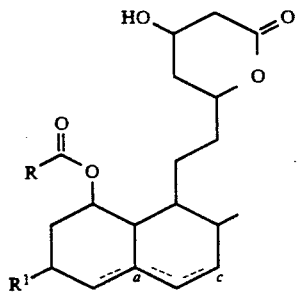

where R is similar to the corresponding group in the compound described above, $R^1$ is a group of formula $CH_2OH$, $CH_2OCOR^3$, $CO_2R^4$ or $CONR^6R^7$ wherein $R^3$, $R^4$, $R^6$ and $R^7$ can cover a range of alkyl, alkoxy or aryl groups, an the dotted lines represent single or double bonds.

The compound disclosed have been generally obtained by fermentation of a suitable microorganism, or have been chemically derived from compounds obtained from such fermentations. However, a procedure based totally on chemical synthesis would have significant advantages over a fermentation procedure on grounds of flexibility, yield, ease of purification and hence cost.

WO-A-9100280 discloses the total synthesis of a group of HMG-CoA reductase inhibiting mevinic acids. Specifically, this publication describes the synthesis of compounds of the general formula:

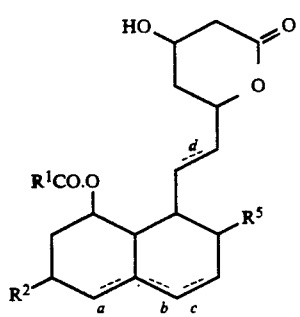

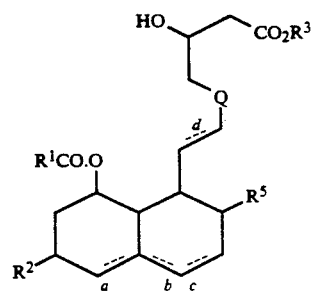

wherein:

$R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group;

$R^2$ represents a $C_{1-8}$ alkyl, $C_{2-8}$ alkenyl, $C_{2-8}$ alkynyl, group or a $C_{1-5}$ alkyl, $C_{2-5}$ alkenyl, or $C_{2-5}$ alkynyl group substituted with a substituted phenyl group;

$R^3$ represents a hydrogen atom or a substituent $R^4$ or M;

$R^4$ represent a $C_{1-5}$ alkyl group, or a $C_{1-5}$ alkyl group substituted with a group chosen from substituted phenyl, dimethylamino and acetylamino;

$R^5$ represents a hydrogen atom or a methyl or ethyl group, except that when $R^2$ is methyl then $R^5$ is not methyl;

M represent a cation capable of forming a pharmaceutically acceptable salt;

Q represents C=O or CHOH; and each of a, b, c, and d is independently a single or double bond except that when a and c are double bonds then b is a single bond.

In particular the document describes the synthesis of (1S, 2S, 4aR, 6S, 8S, 8aS, 4'R, 6'R)-6'-{2-(1,2,4a,5,6,7,8,8a-octahydro-2-methyl-8-[(2''-dimethyl-1''-oxobutyl)-oxy]-6-[(E)-prop-1-enyl]-1-naphthalenyl)ethyl}-tetrahydro-4'-hydroxy-2H-pyran-2'-one which has the structure:

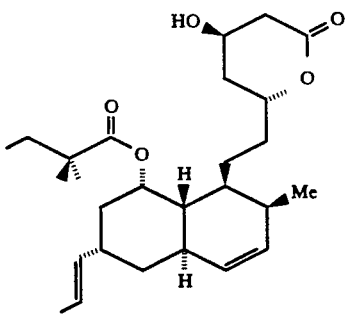

Pioneering as the work disclosed in WO-A-9100280 is, however, there is still room for further improvement in the synthetic methodology used, not least to enable the synthesis to be readily scaled up from the laboratory to pilot plant or production scale.

One of the steps used in the synthesis is the conversion of an aldehyde substituent on the decalin ring to an alkenyl substituent. In WO-A-9100280, this conversion is carried out either by a route involving sulphone derivatives and mercury amalgam, which because of its high toxicity is obviously unsuitable for use on a large scale, or by the Wittig reaction. Although the Wittig reaction proceeds satisfactorily, the reaction temperature must be kept at about −78° C. to avoid decomposition of the ylid starting material.

It has now been found that other conditions and reactants may be used to enable the reaction to proceed at or near room temperature.

SUMMARY OF THE INVENTION

According to a first aspect of the invention there is provided a process for the preparation of a compound of general formula I

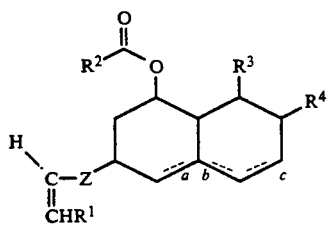

Wherein
$R^1$ represents a $C_{1-8}$ alkyl group;
$R^2$ represents $C_{1-8}$ alkyl, $C_{2-8}$ alkenyl, $C_{2-8}$ alkynyl, $C_{3-8}$ cycloalkyl($C_{1-8}$)alkyl, $C_{1-8}$ hydroxyalkyl, $C_{1-8}$ alkylthio, phenyl or substituted phenyl;
$R^3$ represents $C_{1-8}$ alkyl, $C_{2-8}$ alkenyl, $C_{2-8}$ alkynyl, $CO_2(C_{1-8})$alkyl, $CO_2(C_{2-8})$alkenyl, $C_{1-8}$ alkylthio, $(C_{1-2})$ alkyl $CO_2(C_{1-8})$alkyl or $C_{1-8}$ aldehydroalkyl where the aldehyde function is protected by a suitable protecting group (for example, an acetal such as a dimethyl acetal);
$R^4$ represents a hydrogen atom, $C_{1-8}$ alkyl or $C_{2-8}$ alkenyl;
Z represents a group $(CH_2)_n$ or a branched alkyl chain;
n is 0 to 8;
and each of a, b and c is independently a single or a double bond;
the process comprising reacting a compound of general formula II

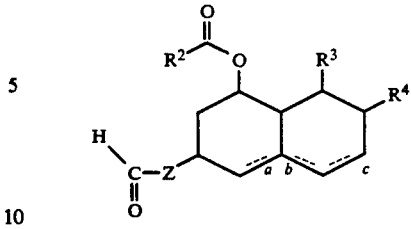

wherein $R^2$, $R^3$, $R^4$, Z, a, b and c are as defined in general formula I; with a compound of general formula III $$CHI_2R^1 \qquad (III)$$

wherein $R^1$ is as defined in general formula I;
in the presence of meal ions such as chromium ions.

As used herein the term "$C_{1-8}$ alkyl" refers to a straight chain or branched chain hydrocarbon group having from one to eight carbon atoms. Illustrative of such alkyl groups are methyl, ethyl, propyl, isopropyl, butyl, isobutyl, sec-butyl, tertbutyl, pentyl, neopentyl, hexyl, heptyl and octyl.

As used herein the term "$C_{2-8}$ alkenyl" refers to straight chain or branched chain hydrocarbon groups having from two to eight carbon atoms and having in addition one or more double bonds, each of either E or Z stereochemistry where applicable. This term would include for example, vinyl, 1-propenyl, 1- and 2-butenyl and 2-methyl-2-propenyl.

As used herein, the term "$C_{2-8}$ alkynyl" refers to a straight or branched chain hydrocarbon group having from one to eight carbon atoms and having in addition one or more triple bonds. This term would include for example, proparyl and 1- and 2- butynyl.

As used herein the term "$C_{1-8}$ hydroxyalkyl" refers to straight chain or branched chain alkyl groups having from one to eight carbon atoms, ad in addition having one or more hydroxyl groups. Illustrative of such hydroxyalkyl groups are hydroxymethyl, hydroxyethyl, and hydroxypropyl.

As used herein the term "$C_{1-8}$ alkylthio" refers to straight chain or branched chain alkyl groups having from one to eight carbon atoms, and in addition having one or more thio groups. Illustrative of such alkylthio groups are thiomethyl, thioethyl, and thiopropyl.

As used herein the term "$C_{1-8}$ aldehydroalkyl" refers to straight chain or branched chain alkyl groups having from one to eight carbon atom, and in addition having one or more aldehyde groups. Illustrative of such aldehydroalkyl groups are ethanal, and propional.

As used herein, the term "$C_{3-8}$ cycloalkyl" refers to an alicyclic group having from 3 to 8 carbon atoms. Illustrative of such cycloalkyl groups are cyclopropyl, cyclobutyl, cyclopentyl and cyclohexyl.

The term "substituted" as applied to a phenyl or other aromatic ring, means substituted with up to four substituents each of which independently may be $C_{1-6}$ alkyl, $C_{1-6}$ alkoxy, hydroxythiol, amino, halo (including fluoro, chloro, bromo and iodo) trifluoromethyl or nitro.

As mentioned above, one advantage of this olefination reaction is that it can be carried out at room temperature whereas for the Wittig reaction which was used previously it was necessary to cool the reaction mixture to −78° C. which is a marked disadvantage, especially if the reaction is to be carried out on a large scale.

Although the ions of other metals can be use in the reaction, it appears that the olefination proceeds most effectively in the presence of chromium ions such as chromium (II) ions. A suitable source of chromium (II) ions is chromium (II) chloride. Alternatively chromium (II) ions can be obtained by the reduction of a chromium (III) compound, for example chromium (III) chloride using a mild reducing agent such as zinc.

A further advantage of the use of this olefination reaction is that the ration of E and Z products can be controlled simply by changing the solvent in which the reaction is carried out. Suitable solvents for the reaction include tetrahydrofuran and dimethylformamide and it has been found that tetrahydrofuran is a particularly useful solvent if a large proportion of the E isomer product is required. A ratio of E:Z isomers of as high as 15:1 has been achieved when the reaction is carried out in tetrahydrofuran, whereas with the Wittig reaction, the predominant product is the Z isomer.

The use of 1,1-diiodoalkanes in the presence of chromium (II) ions in the olefination of simple aldehydes is known as the Takai reaction (J. Am. Chem. Soc., (1987), 109, 951–953, Takai, K. et al).

While Takai et al reacted aldehydic hydrocarbons with 1,1-diiodoalkanes, it has now been discovered that the Takai reaction can be applied to much more complex aldehydes, including these substituted with polar substitutes and comprising a bulky nucleus. Surprisingly, neither electronic effects or steric considerations have a detrimental influence on the progress of the reaction. The reaction has in fact proved to be remarkably successful, with yields of over 80% being achieved.

Compounds of general formulae I and II are new and constitute second and third aspects of the invention. Preferred compounds include those in which, independently or in any compatible combination:

$R^2$ represents $C_{1-8}$ alkyl, $C_{2-8}$ alkenyl, $C_{2-8}$ alkynyl or $C_{1-8}$ hydroxyalkyl;

$R^3$ represents $CO_2C_{1-8}$ alkyl;

$R^4$ represents a methyl group;

Z is $(CH_2)_n$;

n is 0; and a and b are single bonds and c is a double bond; and in compounds of formula I, $R^1$ is a methyl group.

A particularly preferred compound of formula I is ethyl (1S, 2S, 4aR, 6S, 8S, 8aS)-1,2,4a,5,6,7,8,8a-octahydro-6-[(E)-prop-1-enyl]-2-methyl-8-(2,2-dimethylbutyryloxy) naphthalene-1-carboxylate.

A particularly preferred compound of formula II is ethyl(1S, 2S, 4aR, 6S, 8S, 8aS)-1,2,4a,5,6,7,8,8a-octahydro-6-formyl-2-methyl-8-(2,2-dimethylbutyryloxy) naphthalene-1-carboxylate.

Compounds of general formula I in which $R^3$ has an ester group can be reduced to give compounds of general formula IV

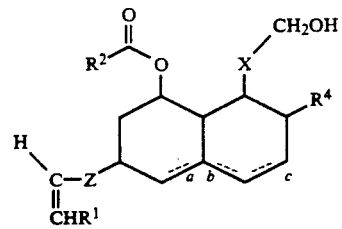

wherein $R^1$, $R^2$, $R^4$, Z, a, b and c are as defined in general formula I;

X is $(CH_2)_m$ or a branched alkyl chain; and m is 0 to 2 using a reducing agent such as lithium aluminium hydride or lithium borohydride or alkyl derivatives of either of them. A particularly suitable reducing agent for the reaction is lithium triethylborohydride and it is preferred that the reaction be carried out in a solvent such as tetrahydrofuran at a temperature of between $-20°$ C. and room temperature. The reaction proceeds particularly satisfactorily at about $0°$ C.

Compounds of formula IV wherein X is $(CH_2)_m$ and m is 0 are known, however other compounds of formula IV are new and all of the compounds of formula IV are useful intermediates in the preparation of mevinic acids.

Compounds of formula II can be prepared from compounds of formula V

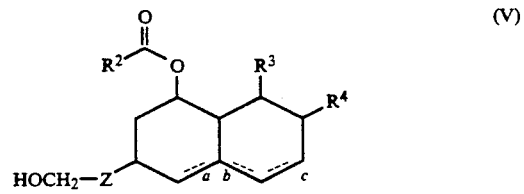

wherein $R^2$, $R^3$, $R^4$, Z, a, b and c are as defined in general formula I;

by oxidation with a mild oxidizing agent which may be for example pyridinium dichromate in the presence of activated molecular sieves and acetic acid. The reaction can be performed in any suitable inert, aprotic solvent such as dichloromethane and will generally be carried out under an inert atmosphere such as argon.

Compounds of formula V can be prepared from compounds of formula VI

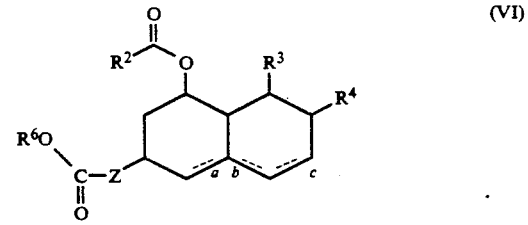

wherein $R^2$, $R^3$, $R^4$, Z, a, b and c are as define din general formula I and $R^6$ is a $C_{1-8}$ alkyl straight chain alkyl group;

by selective reduction of the ester group attached to the 6-position of the decalin ring system.

In principle, selective reduction can be achieved by protecting any other groups liable to reduction, such as the ester group at the 8-position and the ester group at the 1-position in preferred embodiments of the invention. Reduction made selective by protection in this way is largely conventional, and is the route followed in WO-A-9100280.

It has now been discovered that, possibly due to unusual steric factors resulting from the spatial configuration of the decalin-based ring system it is not necessary to protected ester, or even other vulnerable groups at positions other than the 6-position. Direct reaction with a reducing agent, without protection of other groups, results in selective reduction ah the 6-position automatically. While steric actors are suspected to be the reason for this quite unexpected selectivity, the precise mechanism is not clear. This selective reduction of an ester group in a compound containing two or more ester groups forms a further aspect of the invention, according to which there is provided a process for the selective reduction of a compound of general formula VI as defined above, the process comprising reacting a compound of general formula VI, in which at least the ester groups at the 6 and 8-position are unprotected, with a reducing agent.

In order to promote the elective reaction of the ester at the 6-position, rather than the ester group at the 8-position, $R^2$ (at the 8-position) will generally be a more bulky group than $R^6$ (at the 6-position). Suitable reducing agents for this reaction include complex hydrides such as lithium aluminium hydride, lithium borohydride or their alkyl derivatives; a particularly preferred agent is lithium triethylborohydride.

The reaction can be performed in any suitable aprotic, inert solvent with tetrahydrofuran being preferred.

Even when the $R^3$ substituent (at the 1-position) contains an ester group, the reaction still proceeds in a high yield and with selective reduction of the ester group attached to the 6 -position of the decalin ring. A particularly high degree of selectivity is obtained when $R^3$ is an ester group in which the ester carbon is directly connected to the decalin ring and in this case, yields of over 95% of the product of general formula V have been obtained.

Compounds of general formulae V nd VI are novel and comprise further aspects of the invention. Preferred compounds include those in which, independently or in any compatible combination:
$R^2$ represents $C_{1-8}$ alkyl, $C_{2-8}$ alkenyl, $C_{2-8}$ alkynyl or $C_{1-8}$ hydroxyalkyl;
$R^3$ represents $CO_2(C_{1-8})$alkyl;
$R^4$ represents a methyl group;
Z is $(CH_2)_n$;
n is 0; and
a and b are single bonds and c is a double bond; and in compounds of general formula VI, $R^6$ is methyl.

A particularly preferred compound of general formula V is:
ethyl (1S, 2S, 4aR, 6S, 8S, 8aS)-1,2,4a,5,6,7,8,8a-octahydro-6-methoxycarbonyl-2-methyl-8-(2,2-dimethylbutyryloxy) napthalene-1-carboxylate.

A particularly preferred compound of formula VI is;
ethyl (1S, 2S, 4aR, 6S, 8S, 8aS)-1,2,4a,5,6,7,8,8a-octahydro-6-methoxycarbonyl-2-methyl-8-(2,2-dimethylbutyryloxy) napthalene-1-carboxylate.

Compounds of general formula VI can be prepared from compounds of general formula VII

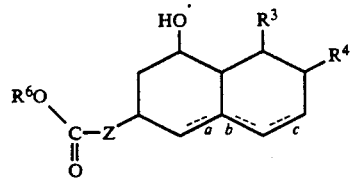

VII wherein $R^3$, $R^4$, Z, a, b and c are as defined in general formula I and $R^6$ is $C_{1-8}$ alkyl;
by acylation with an appropriate acylating agent, which may be an acid halide of general formula VIIa $$R^2COX \qquad (VIIIa)$$

wherein $R^2$ is as defined in general formula I and X is Cl or Br.

The reaction may be carried out in an aprotic solvent such as tetrahydrofuran in the presence of a suitable base, for example triethylamine.

Alternatively, the acylating agent may be an acid anhydride of general formula VIIb in the presence of pyridine.

$$(R^2CO)_2O \qquad (VIIIb)$$

wherein $R^2$as is defined in general formula I. alternatively, and particularly in cases where compounds of general formulae VIIIa and VIIIb are unstable, a carboxylic acid of general formula VIIIc may be used as an acylating agent.

$$R^2CO_2H \qquad (VIIIc)$$

wherein $R^2$ is as defined in general formula I. The reaction should preferably be carried out in the presence of a coupling agent such as 1,3-dicyclohexylcarbodiimide in pyridine or in an aprotic solvent such as tetrahydrofuran. Preferably, an activating agent such as diemthylaminopyridine is also present and a base such as triethylamine may also be used. A particularly suitable acylating agent for this reaction is dimethylbutyryl chloride in pyridine and the reaction temperature is ideally abut 90° C.

Compounds of formula VII are known and can easily be prepared by a person skilled in the art.

The invention also provides a method of preparing a compound of general formula IV from a compound of general formula VII using, sequentially, the steps described above. This method has considerable advantages over the method described in WO-A-9100280, not only because of the advantages mentioned in connection with the intermediate conversion of a compound of general formula II to a compound of general formula I, but also because the ester at the 8-position of the ring does no ave to be protected in the route of this invention and therefore there are fewer steps in the synthesis thus simplifying the process and increasing the overall yield.

In still another aspect of the invention, there is provided a method for the preparation of compound of general formulae IX and X:

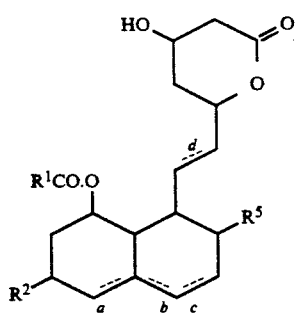

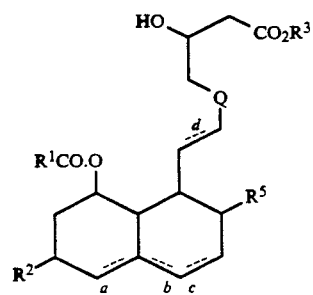

wherein:

$R^1$ represents a $C_{1-8}$ alkyl, $C_{3-8}$ cycloalkyl, $C_{3-8}$ cycloalkyl($C_{1-8}$)alkyl, $C_{2-8}$ alkenyl, or $C_{1-6}$ alkyl substituted phenyl group;

$R^2$ represents a $C_{1-8}$ alkyl, $C_{2-8}$ alkenyl, $C_{2-8}$ alkynyl, group or a $C_{1-5}$ alkyl, $C_{2-5}$ alkenyl, or $C_{2-5}$ alkynyl group substituted with a substituted phenyl group;

$R^3$ represents a hydrogen atom or a substituent $R^4$ or M;

$R^4$ represents a $C_{1-5}$ alkyl group, or a $C_{1-5}$ alkyl group substituted with a group chosen from substituted phenyl, dimethylamino and acetylamino;

$R^5$ represents hydrogen atom or methyl or ethyl group, except that when $R^2$ is methyl then $R^5$ is not methyl;

M represents a cation capable of forming a pharmaceutically acceptable salt;

Q represents C=O or CHOH; and each of a, b, c, and d is independently a single or double bond except that when a and c are double bonds then b is a single bond;

the method comprising converting a compound of general formula VII to a compound of general formula IV by the method described above, followed by converting a compound of general formula IV to a compound of general formula IX or X by an appropriate method.

As mentioned above, compounds of general formulae IX and X were described in WO-A-9100280 and can be prepared from compounds of formula IV by the route described in that document.

A particularly preferred compound which can be prepared by this route is:

(1S, 2S, 4aR, 6S, 8S, 8aS, 4'R, 6'R)-6'-(2-(1,2,4a,5,6,7,8,8 a-octohydro-2-methyl-8-[(2'',2''-dimethyl-1''-oxobutyl)-oxy]-6-[(E)-prop-1-enyl]-1-naphthalenyl)-ethyl}-tetrahydro-4'-hydroxy-2H-pyran-2'-one which has the formula

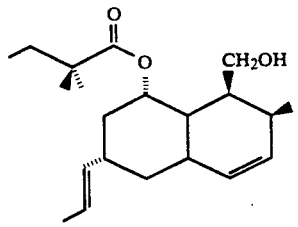

and which can be prepared from (1S, 3S, 4aR, 7S, 8S, 8aS)-1,2,4,4a,5,6,7,8,8a-octahydro-8-hydroxymethyl-7-methyl-3-[(E)-prop-1-enyl]-1-naphthalenyl 2,2-dimethylbutyrate, a compound of general formula IV which has the structure:

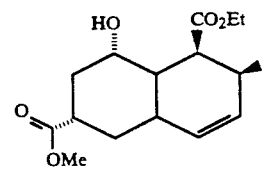

DESCRIPTION OF THE PREFERRED EMBODIMENT the following example, which is for the purposes of illustration only, shows the synthesis of a compound of general formula IV starting from a compound of general formula VII.

In each of the steps: organic solutions were dried over magnesium sulphate.

THF refers to tetrahydrofuran.

NMR spectra were recorded at ambient temperature in deuteriochloroform at 250 MHz for proton and 62.5 MHz for carbon unless noted otherwise. All chemical shifts are given in parts per million relative to trimethylsilane.

Infra red spectra were recorded at ambient temperature in solution in chloroform, or in the solid state in a potassium bromide disc.

EXAMPLE

Step 1

Ethyl (1S, 2S, 4aR, 6S, 8S, 8aS)-1,2,4a,5,6,7,8,8a-octahydro-8-hydroxy-6-methoxycarbonyl-2-methyl-naphthalene-1-carboxylate.

Sodium bis(trimethylsilyl)amide (1.0M in tetrahydrofuran; 144.8 mmol) was added via cannula to a stirred solution of (+) ethyl (1S, 2S, 4aR, 6S, 8S, 8aS)-1,2,4,4a,5,6,7,8,8a-octahydro-2-methyl-6,8naphthalenecarbolactone-1-carboxylate, (37.9 g), 143.4 mmol) in dry methanol (1.6L) and cooled to between −15° C,. to −20° C. under argon. The cold solution was stirred for 2 hours then a saturated solution of ammonium chloride (400 mL) was added in several portion. The mixture was allowed to warm to +15° C., then the methanol was evaporated under reduced pressure and the thick aqueous residue extracted with diethyl ether (1×500 mL, 2×250 mL). The combined diethyl ether extracts were washed successively with 2M aqueous hydrochloric acid (200 mL), water (200 mL), and brine (200 mL) then dried and evaporated under reduced pressure. The residue was crystallised from diethyl ether/hexane, to give three crops of the hydroxy ester product (25.8 g, 61%).

delta $_H$ 5.60 (1H, ddd, J 9.8, 4.5 and 2.7 Hz), 5.40 (1H, d, J 9.8 Hz), 4.28 (1H, m), 4.15 (2H, m), 3.73 (3H, s), 3.51 (1H, d, J 6.4 Hz), 2.90 (1H, dd, J 11.6, 6.0 Hz), 2.84 (1H, m), 2.62 (1H, m), 2.38–2.30 (2H, m), 2.16–2.10(1H, m), 1.82 (1H, ddd, 15.1, 6.1, 3.5 Hz), 1.55–1.35 (2H, m), 1.28 (3H, t, J 7.1 Hz), 0.91 (3H, d, J 7.2 Hz)

Step 2

Ethyl (1S, 2S, 4aR, 6S, 8S, 8aS)-1,2,4,4a,5,6,7,8,8a-octahydro-6-methoxycarbonyl-2-methyl-8-(2,2-dimethylbutyryloxy) naphthalene-1-carboxylate.

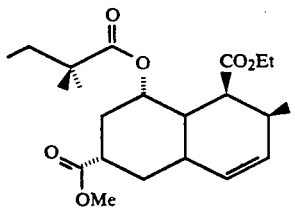

A solution of the alcohol from step 1 (37.5 g, 127 mmol), 2,2-dimethylbutyryl chloride (68.2, 453 mmol) and 4-dimethylamino pyridine (2.1 g, 17 mmol) in pyridine (1000 mL) was stirred at 90° C. (oil-bath temperature) for 16 hours. The dark reaction mixture was concentrated to 100 mL and then partitioned between dichloromethane (2×500 mL) and 2M aqueous hydrochloric acid (500 mL). The combined organic layers were washed with water (2×400 mL) and saturated aqueous sodium bicarbonate solution (500 mL), then dried and evaporated under reduced pressure. The residual brown oil (52.3 g was purified by chromatography on silica eluting with hexane: ethyl acetate (9:1) affording the product as a pale brown oil (46.0 g, 92%).

TLC: RF 0.33 (hexane: ethyl acetate, 4:1).

delta $_H$ 5.55 (1H, m), 5.47 (1H, d, J 10.3 Hz), 5.43 (1H, m), 4.11 (2H, q, J 7.2 Hz), 3.67 (3H, s), 2.73–2.46 (5H, m), 2.32 (1H, br d, J 13.5 Hz), 1.91 (1H, ddd, J 15.2, 7.2, 2.9 Hz), 1.7–1.61 (1H, m), 1.49 (2H, q, J 7.5 Hz), 1.24 (3H, t, J 7.2 Hz), 1.31–1.19 (1H, m), 1.09 (3H, s), 1.07 (3H, s), 0.89 (3H, d, J 6.7 Hz), 0.81 (3H, t, J 7.5 Hz)

Step 3

Ethyl (1S, 2S, 4aR, 6S, 8S, 8aS)-1,2,4a,5,6,7,8,8a-octahydro-6-hydroxymethyl-2-methyl-8-(2,2-dimethylbutyryloxy) naphthalene-1-carboxylate.

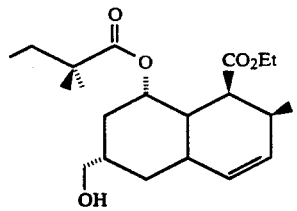

Lithium triethylborohydride (1M solution in THF; 337 mmol; 2.1 equivalents) was added over approx 20 minutes to a stirred solution of the triester from step 2 (63.2 g, 160.5 mmol) in dry THF (800 mL) under argon, at between 5° C. and 0° C. After 1 hour, saturated ammonium chloride solution (250 mL) was added and the mixture allowed to warm to room temperature, with stirring. The THF was evaporated under reduced pressure and the residue extracted with ethyl acetate (3×300 mL). The combined ethyl acetate extracts were washed vigorously with 2M hydrochloric acid (250 mL), followed by saturated sodium bicarbonate solution (250 mL) and brine (100 mL) and dried. Evaporation under reduced pressure gave a gum, which was dissolved in methanol (250 mL). The solution was heated to approx 50° C., then the methanol evaporated under reduced pressure. The residue was purified by chromatography on silica eluting with ethyl acetate:hexane (1:4 to 1:2) to give the product (10) as a white solid ((56.7 g, 96%).

Tlc: RF 0.21 (30% ethyl acetate/hexane)

delta $_H$ 5.64–5.58 (1H, m), 5.44–5.40 (2H, m), 4.18 4.05 (2H, m), 3.82 (1H, t, J 10.0 Hz), 3.59 (1H, dd, J 10.5, 5.8 Hz), 2.67–2.55 (2H, m), 2.45–2.26 (1H, m), 2.10–1.18 (12H, complex m), 1.15 (3H, s), 1.14 (3H, s), 0.91 (3H, d, J 6.9 Hz), 0.84 (3H, t, J 7.5 Hz)

Step 4

Ethyl (1S, 2S, 4aR, 6S, 8S, 8aS)-1,2,4a,5,6,7,8,8a-octahydro-6-formyl-2-methyl-8-(2,2-dimethylbutyryloxy) naphthalene-1-carboxylate.

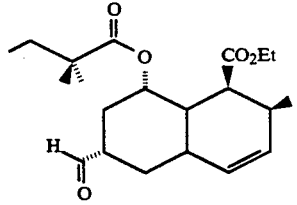

A solution of the alcohol from step 3 (56.7 g, 154.8 mmol) in dry dichloromethane (2×400 mL) was added via cannula to a stirred mixture of finely ground pyridinium dichromate (86.8 g, 230.8 mmol) and freshly activated finely ground 3A molecular sieves (28.4 g) under argon. The mixture was cooled in a cold-water bath and dry acetic acid (15.5 mL) added slowly. After 80 minute, diethyl ether (3 L) was added and the mixture filtered through Kieselguhr (to remove most of the insoluble chromium slats) before passing the filtrate down a Florisil (60–100 mesh) column. (The word FLORISIL is a trade mark). The column was eluted with excess diethyl ether, which was evaporated and the residue azeotroped with toluene to leave the aldehyde as a pale yellow oil, which crystallised (55.5 g, 98.4%)

Tlc: RF 0.37 (SiO₂ 30% ethyl acetate/hexane).

delta $_H$ 9.65 (1H, d, J 1 Hz), 5.62–5.44 (3H, m), 4.12 (2H, q, J 7.1 Hz), 2.59–2.24 (7H, m), 2.08–1.99 (1H, m), 1.66 (1H, td, J 10.9, 1.6 Hz), 1.49 (2H, qd, J 7.7, 2.3 Hz), 1.23 (3H, t, J 7.4 Hz), 1.09 (3H, s), 1.07 (3H, s), 0.89 (3H, d, J 6.8 Hz), 0.80 (3H, t, J 7.4 Hz)

Step 5

Ethyl (1S, 2S, 4aR, 6S, 8S, 8aS)-1,2,4a,5,6,7,8,8a-octahydro-2-methyl-8-(2,2-dimethylbutyryloxy)-6-[(E)-prop-1-enyl]naphthalene-1-carboxylate.

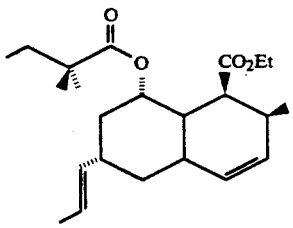

THF (100 mL) was added to chromium (II) chloride (112.2 g, 0.91 mol) under an argon atmosphere. After stirring the mixture until a fine suspension resulted, a solution of the aldehyde from step 4 (41.6 g, 0.11 mol) and 1,1-diiodoethane (64.4 g, 0.23 mol) in THF (500 mL) was added. The reaction mixture was stirred for 15 ours, then water (750 ml) was added and stirring continued for 5 minutes. The THF was removed under reduced pressure and the aqueous mixture extracted with ether 3×500 mL). The combined ethereal layers were washed with brine (500 mL) and dried and evaporated under reduced pressure, leaving a green oil. This was purified by chromatography on silica eluting with hexane: ethyl acetate, (19:1 to 9:1), giving the product as a colourless oil (35:1 g, 82%).

Tlc: RF 0.34 (hexane: ethyl acetate, 9:1)

delta $_H$ 5.83–5.73 (1H, m), 5.63–5.57 (1H, m), 5.46–5.32 (3H, m), 4.18–4.06 (2H, m), 2.68 (1H, dd, J 11.4, 5.9 Hz), 2.70–2.43 (3H, m), 2.0–1.37 (7H, complex m), 1.63 (3H, dt, J 6.5, 1.1 Hz), 1.24 (3H, t, 7.0 Hz), 1.15 (3H, s), 1.14 (3H, s), 0.91 (3H, d, J 6.9 Hz), 0.83 (3H, t, J 7.4 Hz)

Step 6

(1S, 3S, 4aR, 7S, 8S, 8aS)-1,2,4,4a,7,8,8a-octahydro-8-hydroxymethyl-7-methyl-3-[(E)-prop-1-enyl]-1-naphthalenyl 2,2-dimethylbutyrate.

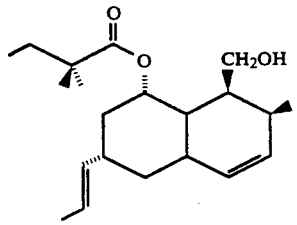

A solution of the ester from step 5 (35.1 g) 93.3 mmol) was stirred in THF (350 mL) at −78° C. while a solution of lithium triethylborohydride in THF (1M, 280 mL, 280 mmol) was added. The reaction mixture was allowed to warm to 4° C. and left for 14 hours. Saturated aqueous ammonium chloride solution (500 mL) was cautiously added, the THF removed under reduced pressure and the resulting aqueous mixture extracted with ethyl acetate (3×500 mL). The combined organic layers wee washed with 2M aqueous hydrochloric acid solution (500 mL) and brine (250 mL), ad then dried and evaporated under reduced pressure. The residue was dissolved in methanol (100 mL) and the solution heated at 50° C. for 10 minutes and then evaporated. This procedure was repeated once the residual pale yellow oil (29.6 g) was purified by chromatography on silica eluting with hexane: ethyl acetate, (gradient from 85:15: to 0:100, affording the product as a white solid (18.1 g, 58%), followed by the over-reduction product.

Tlc: RF 0.54 (hexane:ethyl acetate, 1:1.

delta $_H$ 5.77 (1H, ddq, J 15.2, 8.2, 1.6 Hz), 5.65 (1H, ddd, 9.8, 4.8, 2.6), 5.45–5.31 (2H, m), 5.04 (1H, m), 3.64 (1H, dd, J 10.4, 4.85 Hz), 3.49 (1H, t, J 9.8 Hz), 2.58 2.50 (3H, m), 2.01–1.89 (2H, m), 1.8–1.22 (10H, complex m), 1.17 (3H, s), 1.16 (3H, s), 0.94 (3H, d, J 6.9 Hz), 0.86 (3H, t, J 7.1 Hz)

It can therefore be seen that the invention provides a simple and convenient route of the production of compounds of general formula IV which are useful intermediates in the production of mevinic acids.

What is claimed is:

1. A compound of general formula I

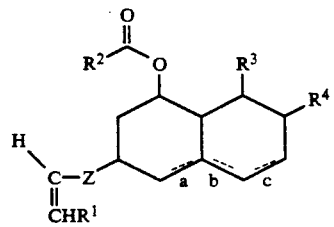

wherein R¹ represents a $C_{1-8}$ alkyl group;

R² represents $C_{1-8}$ alkyl, $C_{2-8}$ alkenyl, $C_{2-8}$ alkynyl, $C_{3-8}$ cycloalkyl $(C_{1-8})$alkyl, $C_{1-8}$ hydroxyalkyl, $C_{1-8}$ alkylthio, phenyl or substituted phenyl group wherein the phenyl is substituted by one to four substituents each of which independently is $C_{1-6}$ alkyl, $C_{1-6}$ alkoxy, hydroxy thiol, amino, halogen, trifluoromethyl or nitro;

R³ represents $C_{1-8}$ alkyl, $C_{2-8}$ alkenyl, $C_{2-8}$ alkynyl, $CO_2(C_{1-8})$alkyl, $CO_{2(2-8)}$ alkenyl, $C_{1-8}$ alkylthio, $(C_{1-2})$ alkyl $CO_2(C_{1-8})$ alkyl or $C_{1-8}$ aldehydroalkyl where the aldehyde function is protected by a dimethyl acetal protecting group.

R⁴ represents a hydrogen atom, $C_{1-8}$ alkyl or $C_{2-8}$ alkenyl;

Z represents a group $(CH_2)_n$ or a branched alkyl chain; n is 0 to 8 and each of a, b and c s independently a single r a double bond except that when a or c is a double bond, b is a single bond.

2. Ethyl (1S, 2S, 4aR, 6S, 8S, 8aS)-1,2,4a,5,6,7,8,8a-octahydro-6-[(E)-prop-1-enyl]-2methyl-8-(2,2-dimethylbutyryloxy)-naphthalene-1-carboxylate.

* * * * *